United States Patent [19]

Cantillo et al.

[11] Patent Number: 5,091,449
[45] Date of Patent: Feb. 25, 1992

[54] ALPHA-(2,4-DIHYDROXY)PHENYL N-PHENYL NITRONE AND ITS USE IN THE MODIFICATION OF DIENE CONTAINING POLYMERS

[75] Inventors: Jose Cantillo, Miami, Fla.; Robert W. Strozier, Akron; William P. Francik, Bath, both of Ohio

[73] Assignee: The Goodyear Tire & Rubber Company, Akron, Ohio

[21] Appl. No.: 563,028

[22] Filed: Aug. 2, 1990

[51] Int. Cl.$^5$ .............................................. C08K 5/34
[52] U.S. Cl. .................... 524/100; 524/248; 524/249; 524/574; 524/575; 524/575.5; 525/343
[58] Field of Search ............... 524/236, 248, 249, 100

[56] References Cited

U.S. PATENT DOCUMENTS

| 3,390,133 | 6/1968 | Breslow | 260/75 |
| 3,390,204 | 6/1968 | Breslow | 260/837 |
| 3,576,908 | 4/1971 | Brack | 260/858 |
| 3,792,031 | 2/1974 | Udding | 260/94.7 N |
| 3,903,049 | 9/1975 | Saltman et al. | 260/47 UA |
| 3,917,700 | 11/1975 | Auerbach | 260/566 R |
| 3,985,709 | 10/1976 | Saltman et al. | 260/47 UA |
| 4,672,088 | 6/1987 | Scott et al. | 524/236 |

FOREIGN PATENT DOCUMENTS 788000 6/1968 Canada .
2137619 10/1984 United Kingdom .
8403883 10/1984 World Int. Prop. O. .

OTHER PUBLICATIONS

Boyland et al, "Notes", pp. 3141-3144, 578 (1963).
Scott et al, "European Polymer Journal", vol. 14, pp. 905-912 (1978).
Scott et al, "European Polymer Journal", vol. 14, pp. 39-43 (1978).
Nethsinghe et al, "Rubber Chemistry and Technology", vol. 57, pp. 779-791 (1984).
Tada et al, "Journal of Applied Polymer Science", vol. 15, pp. 117-128 (1971).
Hamer et al, vol. 64, Chem. Res., pp. 473-495 (1964).

Primary Examiner—Joseph L. Schofer
Assistant Examiner—Mark Sweet
Attorney, Agent, or Firm—Bruce J. Hendricks

[57] ABSTRACT

The present invention relates to a mononitrone of the formula:

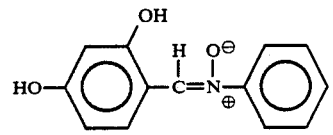

The amount of alpha-(2,4-dihydroxy)phenyl N-phenyl nitrone which is used in the modification of a diene containing polymer may range from about 0.1 to about 30 percent by weight of said polymer. The modified polymers exhibit improved tear properties as measured by Strebler adhesion values.

12 Claims, No Drawings

ALPHA-(2,4-DIHYDROXY)PHENYL N-PHENYL NITRONE AND ITS USE IN THE MODIFICATION OF DIENE CONTAINING POLYMERS

BACKGROUND OF THE INVENTION

U.S. Pat. No. 3,792,031 relates to a process for the modification of elastomeric isoprene polymers. The process includes reacting an isoprene polymer with from about 0.01 to 5 percent by weight of a mononitrone at temperatures of from about 60° C. to about 200° C. Examples of mononitrones listed in this patent are alpha-phenyl-N-phenyl nitrone and alpha(4-hydroxy)-phenyl-N-phenyl nitrone. This patent teaches that the process of modification results in isoprene elastomers having improved green strength.

U.S. Pat. No. 3,985,709 relates to polymeric compositions which are the reaction product of an unsaturated polymer and a mononitrone further containing a 3-5-di-t-butyl-4-hydroxyphenyl group.

Many rubber articles, principally automobile tires, hoses, belts and the like are reinforced with fibers in cord form. In all such instances, the fiber must be firmly bonded to the surrounding rubber. A frequent problem in making these rubber articles is maintaining good adhesion between the rubber and the reinforcement. A conventional method in promoting the adhesion between the rubber and the reinforcement is to pretreat the reinforcing fiber with a mixture of a rubber latex and a phenol-formaldehyde condensation product wherein the phenol is almost always resorcinol. This is the so-called "RFL" (resorcinol-formaldehyde-latex) method. Another method of promoting such adhesion is to generate the resin in-situ (in the vulcanized rubber/textile matrix) by compounding a vulcanizing rubber stock composition with the phenol/formaldehyde condensation product (hereinafter referred to as the "in-situ method"). The components of the condensation product consist of a methylene acceptor and a methylene donor. The most common methylene donors include N-(substituted oxymethyl) melamine, hexamethylenetetramine or hexamethoxymethylmelamine. A common methylene acceptor is a dihydroxybenzene compound such as resorcinol. The in-situ method has been found to be particularly effective where the reinforcing material is steel wire since pretreatment of the wire with the RFL system has been observed to be largely ineffective.

Resorcinol is known to form a resin network within a rubbery polymer by reacting with various methylene donors. Unfortunately, the use of resorcinol has some inherent disadvantages. Resorcinol is not readily dispersed in rubber and in fact neither the resin, nor the resorcinol become chemically bound to the rubber. Additionally, resorcinol in its raw form is excessively volatile and is potentially toxic, thus posing a health hazard. Another disadvantage in using resorcinol is periodic market shortages of supply.

There have been numerous attempts to replace resorcinol, however, few if any have had much success. For example, in U.S. Pat. No. 4,605,696 there is disclosed a method for enhancing adhesion of rubber to reinforcing materials through the use of phenolic esters as the methylene acceptor. These phenolic esters are less volatile than resorcinol, but still offer no readily reactive site for chemically attaching the resin to the rubber.

Therefore, there exists a need to find a suitable replacement for resorcinol in an in-situ resin system while concomitantly improving rubber/reinforcement interaction for increased adhesion in rubber.

SUMMARY OF THE INVENTION

The present invention relates to alpha-(2,4-dihydroxy)phenyl N-phenyl nitrone and its use in the modification of a diene containing polymer.

DETAILED DESCRIPTION OF THE INVENTION

There is disclosed a composition comprising a mononitrone of the formula:

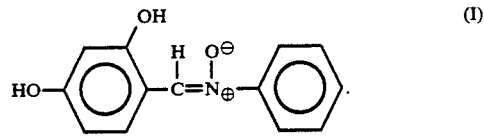

In addition there is disclosed a process for the modification of a diene containing polymer comprising contacting a diene containing polymer with from about 0.1 to about 30 percent by weight of said polymer of alpha-(2,4-dihydroxy)phenyl N-phenyl nitrone.

The above nitrone may be used to modify a diene containing polymer. The term diene containing polymer includes conventional rubbers or elastomers such as natural rubber and all its various raw and reclaimed forms as well as various synthetic unsaturated or partially unsaturated rubbers, i.e., rubber polymers of the type which may be vulcanized with sulfur. Representative of synthetic polymers are the homopolymerization products of butadiene and its homologues and derivatives as for example, methyl butadiene, dimethyl butadiene and pentadiene as well as copolymers such as those formed from a butadiene or its homologues or derivatives with other unsaturated organic compounds. Among the latter are olefins, for example, ethylene, propylene or isobutylene which copolymerizes with isoprene to form polyisobutylene also known as butyl rubber: vinyl compounds, for example, vinyl chloride, acrylic acid, acrylonitrile (which polymerizes with butadiene to form NBR), methacrylonitrile, methacrylic acid, methyl styrene and styrene, the latter compound polymerizing with butadiene to form SBR, as well as vinyl esters and various unsaturated aldehydes, ketones and ethers, e.g., acrolein and vinylethyl ether. Also included are the various synthetic rubbers prepared from the homopolymerization of isoprene and the copolymerization of isoprene with other diolefins and various unsaturated organic compounds. Also included are the synthetic rubbers such as 1,4-cis polybutadiene and 1,4-cis polyisoprene and similar synthetic rubbers which have been developed in recent years, such as EPDM. Such recently developed rubbers include those that have polymer bound functionalities such as antioxidants and antiozonants. These polymer bound materials are known in the art and can have functionalities that provide antidegradative properties, synergism, and other properties. The preferred diene containing polymers for use in the present invention include natural rubber, polybutadiene, synthetic polyisoprene, styrene/butadiene copolymers, isoprene/butadiene copolymers, terpolymers of styrene/isoprene/butadiene, NBR, terpolymers of acrylonitrile, butadiene and styrene and blends thereof.

The amount of nitrone which is to be used in the modification of the diene containing polymer may range from about 0.1 to about 30 percent by weight calculated on the weight of the polymer to be modified. Preferably, from about 2 to about 10 percent by weight of said polymer is used with a range from about 4 to about 8 being most preferred. The modification reaction may be conducted in solution, or under solvent-free conditions (solid state reaction). Preferably, the reaction is conducted in the solid state. The nitrones may be added to the rubbers by any conventional technique such as milling or Banburying.

As disclosed above, the present invention includes a vulcanizable rubber composition comprising: (1) a natural or synthetic rubber, (2) a sulfur vulcanizing agent, (3) from about 0 to about 6 phr of a methylene donor, and (4) from about 0.1 to about 30 phr of alpha-(2,4-dihydroxy)phenyl N-phenyl nitrone. When the methylene donor is present, it is preferably in an amount ranging from about 2 to about 4 phr.

For the purposes of the present invention, alpha-(2,4-dihydroxy)phenyl N-phenyl nitrone may be used as a methylene-acceptor. The term "methylene acceptor" is known to those skilled in the art and is used to describe the reactant to which the methylene donor reacts to form what is believed to be a methylol monomer. The condensation of the methylol monomer by the formation of a methylene bridge produces the resin. The initial reactant that contributes the moiety that later forms into the methylene bridge is the methylene donor wherein the other reactant is the methylene acceptor.

The vulcanizable rubber compositions of the present invention may contain a methylene donor. The term "methylene donor" is intended to mean a compound capable of reacting with the alpha-(2,4-dihydroxy)-phenyl N-phenyl nitrone and generate the resin in-situ. Examples of methylene donors which are suitable for use in the present invention include hexamethylene tetramine, hexaethoxymethyl melamine, hexamethoxymethyl melamine, lauryloxymethylpyridinium chloride, ethoxymethylpyridinium chloride, trioxan hexamethoxymethyl melamine, the hydroxyl groups of which may be esterified or partly esterified, and polymers of formaldehyde such as paraformaldehyde. In addition, the methylene donors may be N-substituted oxamethyl melamines, of the general structural formula:

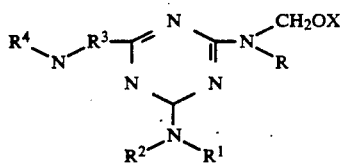

wherein X is an alkyl having 1 to 8 carbon atoms: R, $R^1$, $R^2$, $R^3$ and $R^4$ are individually selected from the group consisting of hydrogen, alkyl having from 1 to 8 carbon atoms, the group —$CH_2OX$ or their condensation products. Specific methylene donors include hexakis(methoxymethyl) melamine, N,N',N"-trimethyl/N,N',N"-trimethylol melamine, hexamethylol melamine, N,N',N"-dimethylol melamine, N-methylol melamine, N,N'-dimethylol melamine, N,N',N"-tris(methoxymethyl) melamine and N,N',N"-tributyl-N,N',N"-trimethylol melamine. The N-methylol derivatives of melamine are prepared by known methods.

The weight ratio of methylene donor to the alpha-(2,4-dihydroxy)phenyl N-phenyl nitrone may vary. Generally speaking, the weight ratio will range from about 1:10 to about 10:1. Preferably, the weight ratio ranges from about 1:3 to 3:1.

The vulcanizable rubber composition of the present invention contains a sulfur vulcanizing agent. Examples of suitable sulfur vulcanizing agents include elemental sulfur, free sulfur, or sulfur donating vulcanizing agents, for example, an amine disulfide, polymeric polysulfide or sulfur olefin adducts. Preferably, the sulfur vucanizing agent is elemental sulfur. The amount of sulfur vulcanizing agent will vary depending on the type of rubber and the particular type of sulfur vulcanizing agent that is used. Generally speaking, the amount of sulfur vulcanizing agent ranges from about 0.1 to about 7 phr with the range of from about 0.5 to about 5 being preferred. The methylene acceptor may be compounded in either the productive or nonproductive stock. Preferably, the methylene acceptor is compounded in the nonproductive stock because more uniform mixing is generally achieved.

In addition to the above, other rubber additives may also be incorporated in the sulfur vulcanizable material. The additives commonly used in rubber vulcanizates are, for example, carbon black, silica, tackifier resins, processing aids, antioxidants, antiozonants, stearic acid, activators, waxes, oils and peptizing agents. As known to those skilled in the art, depending on the intended use of the sulfur vulcanizable material, certain additives mentioned above are commonly used in conventional amounts. Typical amounts of carbon black comprise about 20 to 100 parts by weight of diene rubber (phr), with a range of from 40 to 60 phr being preferred. Typical amounts of tackifier resins comprise about 1 to 10 phr with a range of from 2 to 3 phr being preferred. Typical amounts of processing aids comprising about 1 to 10 phr with a range of from 2 to 5 phr being preferred. Typical amounts of antioxidants comprise 1 to about 10 phr with a range of from 0.5 to 1.0 phr being preferred. Typical amounts of antiozonants comprise 1 to about 10 phr with a range of from 2 to 2.5 being preferred. Typical amounts of stearic acid comprise 0.1 to about 2 phr with a range of from 0.5 to 1 phr being preferred. Typical amounts of zinc oxide comprise 2 to 10 phr with a range of from 3 to 8 being preferred. Typical amounts of waxes comprise 1 to 5 phr, with a range of from 2 to 3 phr being preferred. Typical amounts of oils comprise 5 to 30 phr, with a range of from about 5 to 10 being preferred. Typical amounts of peptizers comprise 0.1 to 1 phr, with a range of from about 0.3 to 0.6 being preferred. Typical additions of silica comprise from about 5 to 25 phr, with a range of from about 10 to 20 phr being preferred. Typical amounts of retarder comprise from 0.05 to 1.0 phr, with a range of from 0.1 to 0.5 being preferred. The presence and relative amounts of the above additives are not an aspect of the present invention.

Accelerators may be used to control the time and/or temperature required for vulcanization and to improve the properties of the vulcanizate. In some instances, a single accelerator system may be used, i.e., primary accelerator. Conventionally, a primary accelerator is used in amounts ranging from about 0.5 to 2.0 phr. In other instances, combinations of two or more accelerators may be used which may consist of a primary accelerator which is generally used in the larger amount (0.5 to 1.0 phr), and a secondary accelerator which is generally used in smaller amounts (0.05-.50 phr) in order to activate and to improve the properties of the vulcanizate. Combinations of these accelerators have been known to produce a synergistic effect of the final properties and are somewhat better than those produced by use of either accelerator alone. In addition, delayed action accelerators may be used which are not effected by normal processing temperatures but product satisfactory cures at ordinary vulcanization temperatures. Suitable types of accelerators that may be used include amines, disulfides, guanidines, thioureas, thiazoles, thiurams, sulfenamides, dithiocarbamates and xanthates. Preferably, the primary accelerator is a sulfenamide. If a secondary accelerator is used, the secondary accelerator is preferably a guanidine, dithiocarbamate or thiuram compound.

Vulcanization of the rubbers containing the nitrone of the present invention may be conducted at conventional temperatures used for vulcanizable materials. For example, temperatures may range from about 100° C. to 200° C. Preferably, the vulcanization is conducted at temperatures ranging from about 110° C. to 180° C. Any of the usual vulcanization processes may be used as heating in a press mold, heating with superheated steam or hot air or at a salt bath.

Example 1

Preparation of alpha-(2,4-dihydroxy)phenyl N-phenyl nitrone 2,4-dihydroxybenzaldehyde (121 grams, 0.88 mole), nitrobenzene (120 grams, 0.97 mole), platinum-on-carbon (5 percent, 0.56 grams) and dimethyl sulfoxide (1.9 grams, 0.02 mole) were placed in ethanol (95 percent, 600 m) in an autoclave. The system was flushed twice with hydrogen gas, charged to a constant pressure of 100 psig $H_2$, and stirred at room temperature for 15 hours. The catalyst was filtered off and the solution was concentrated to a volume of 200 mL using a rotary evaporator. The resultant viscous oil was poured into a mixture of toluene (1 liter) and hexane (500 m), and a light yellow solid precipitated out after cooling. The solid was collected by filtration to give alpha-(2,4-dihydroxy)phenyl N-phenyl nitrone (190 grams, 0.83 mole, 94 percent). MP 131°–134° C.

Example 2

Preparation of Nitrone Modified Polymer

A series of diene containing polymers were modified with alpha-(2,4-dihydroxy)phenyl N-phenyl nitrone. 12 phr of the nitrone was added to the diene containing polymer in a Brabender (140° C.) and allowed to mix for 5 minutes. The modified polymers were reprecipitated and analyzed by UV and elemental analysis. Table I below lists the polymer that was modified and the percent incorporation of the nitrone (weight percent of reacted nitrone).

TABLE I

| Polymer | % Incorporation |
| --- | --- |
| SBR (10% styrene) | 33 |
| PBD (medium vinyl 50%) | 42 |
| PBD (high cis) | 31 |
| Polyisoprene (synthetic) | 53 |
| Natural rubber | 66 |

Example 3

Preparation of Nitrone Modified Polyisoprene

Eight phr of alpha-(2,4-dihydroxy)phenyl N-phenyl nitrone was added to polyisoprene in a Brabender (140° C.) and allowed to mix for 5 minutes. The reaction was 53 percent efficient. The modified polyisoprene was analyzed by UV and elemental analysis.

Example 4

Rubber stocks were prepared which contained a polymer blend of polyisoprene and either high cis polybutadiene, nitrone-modified high cis polybutadiene prepared in Example 2, styrene butadiene rubber (10 percent styrene) or nitrone modified styrene butadiene rubber prepared in Example 2 (10 percent styrene). The rubber stocks were prepared in a Brabender mixer in the first stage of a two stage mix. In addition, the nonproductive rubbers also contained 45 phr of general purpose tread carbon black, 9 phr processing oil, 2 phr diphenylamine antidegradant, 1 phr diarylphenylenediamine antidegradant, 1 phr microcrystalline wax, 3 phr stearic acid and 3 phr sulfur. The productive stock contained the nonproductive stock, 0.8 phr primary accelerator, 0.4 phr secondary accelerator and 1.6 phr sulfur.

Table II sets out the amounts by weight of the polyisoprene, high cis polybutadiene or nitrone-modified high cis polybutadiene, styrene-butadiene rubber and nitrone-modified styrene butadiene rubber. In addition, Table II lists the vulcanizate properties of the various rubber stocks.

Strebler adhesion testing was done to determine the adhesion of the rubber formulation to itself. The Strebler adhesion was determined by pulling the compound away from itself at a right angle to the untorn test specimen with the two ends being pulled apart at a 180° angle to each other using an Instron machine. The area of contact was determined from placement of a Mylar TM sheet between the compounds during cure. A window in the Mylar TM allowed the two compounds to come into contact with each other during testing.

TABLE II

|  | Sample 1 | Sample 2 | Sample 3 | Sample 4 |
| --- | --- | --- | --- | --- |
| Polymer |  |  |  |  |
| Polyisoprene | 25.0 | 25.0 | 25.0 | 25.0 |
| PBD-High Cis (Nitrone Modified via Example 2) | 75.0 |  |  |  |
| PBD-High Cis |  | 75. |  |  |
| SBR (Nitrone Modified via Example 2) |  |  | 75.0 |  |
| SBR |  |  |  | 75.0 |
| Tan Delta [1] |  |  |  |  |
| 0° C. | .157 | .134 | .219 | .228 |
| 60° C. | .167 | .108 | .158 | .140 |
| Strebler Adhesion (Newtons per cm) | 90 | 68 | 82 | 36 |
| % Improvement in Strebler Adhesion | +32 |  | +128 |  |

[1] .5% strain, 0.1 Hz. at room temperature.

As can be seen in Table II, using nitrone modified high cis-polybutadiene and nitrone modified styrene butadiene rubber showed large increases in Strebler adhesion and increases in hysteresis compared to the respective controls.

Example 5

Two rubber stocks were prepared in a Brabender which contained 50 parts of natural rubber, 20 parts high cis polybutadiene and either polyisoprene or 8 percent nitrone modified polyisoprene (prepared in accordance with Example 3). The compounded rubber was typical of a wire coat stock and contained 3 phr of hexamethoxymethylmelamine, 5 parts insoluble sulfur, along with conventional amounts of zinc oxide, carbon black, silica, antiozonant, stearic acid, tackifier, antioxidant, accelerators and retarder.

Table III sets out the relative amounts of the rubbers for each sample. In addition Table III lists the cure behavior and vulcanizate properties of the various rubber stocks.

TABLE III

| | | |
|---|---|---|
| Natural Rubber | 50.00 | 50.00 |
| Polyisoprene (8% Mod.) | 30.00 | |
| Polyisoprene | | 30.00 |
| PBD (High Cis) | 20.00 | 20.00 |
| Productive Tests | | |
| 200% Mod. (mPa) | 11.0 | 6.5 |
| Tensile (mPa) | 12.3 | 18.7 |
| Elongation (%) | 210 | 440 |
| Hardness RT | 79 | 66 |
| 100° C. | 74 | 63 |
| Rebound RT (%) | 47.7 | 47.7 |
| Rebound 100° C. (%) | 60.3 | 61 |
| Rheometer 100 CPM at 150° C. | | |
| S* Min. (dN · M) | 13 | 14 |
| S* Max. (dN · M) | 69 | 57 |
| TC30 (mins.) | 4.5 | 8.5 |
| TC90 (mins.) | 22 | 33 |
| Swat Original (Newtons) | 396 | 322 |
| Strebler to Self Aged 14 Days in Air at 158° F. (Newtons/cm) | 10 | 29 |
| E' 60° C. (mPa) | 25.5 | 19.0 |
| Tan Delta 60° C. | .167 | .182 |

Example 6

The following samples were prepared in order to compare and contrast the properties of rubbers modified with alpha-(2,4-dihydroxy)phenyl N-phenyl nitrone (2,4 DHPPN) versus other mononitrones. The other mononitrones were diphenylnitrone (DPN), (4-hydroxy)phenyl-N-phenylnitrone (4 HPPN) and alpha-(2,5-dihydroxy)phenyl-N-phenylnitrone (2,5 DHPPN). Each nitrone was used to prepare an 8 percent by weight nitrone modified styrene-butadiene rubber (10 percent styrene) in accordance with the general procedure of Example 2. The rubber stocks were prepared in a Banbury and contained 50 parts of the 8 percent nitrone modified styrene-butadiene rubber, 50 parts of natural rubber. The remaining components added in conventional amounts were characteristic of those used in a tread compound. The remaining components included oil, antiozonant, antioxidant, stearic acid, zinc oxide, carbon black, silica, coupling agent, primary accelerator and secondary accelerator. 0.9 parts of sulfur was used.

The various samples were mixed in a Banbury and test samples were milled and cured from the stocks. The samples were tested for Strebler adhesion (newtons per cm). The results from the measurement for tear and processing are listed in Table IV below.

TABLE IV

| Sample No. | Nitrone | Strebler Adhesion | Processing |
|---|---|---|---|
| 1 | 2,4 DHPPN | 166 | Fair |
| 2 | 2,4 DHPPN | 155 | Fair |
| 3 | 2,4 DHPPN | 138 | Fair |
| 4 | 2,5 DHPPN | 150 | Poor |
| 5 | 4 HPPN | N/A | Poor |
| 6 | DPN | 95 | Very Good |

As can be seen above, Samples 1-3 had similar tear properties and had acceptable processing. Samples 4 and 5 had poor processing and resulted in the formulation of crumbs. In fact, the stock of Sample 5 could not be formed into a test sample. Sample 6 had very good processing, however, had unacceptable tear properties.

What is claimed is:

1. A composition comprising a mononitrone of the formula:

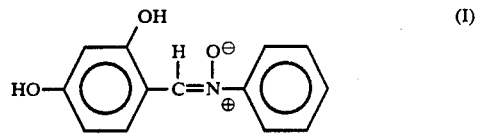

(I)

2. A process for the modification of a diene containing polymer comprising contacting a diene containing polymer with from about 0.1 to about 30 percent by weight of said polymer of alpha-(2,4-dihydroxy)phenyl N-phenyl nitrone.

3. The process of claim 2 wherein from about 3 to about 10 percent by weight of alpha-(2,4-dihydroxy)-phenyl N-phenyl nitrone is used.

4. The process of claim 2 wherein said diene containing polymer is selected from the group consisting of natural rubber, polybutadiene, synthetic polyisoprene, styrene/butadiene copolymers, isoprene/butadiene copolymers, terpolymers of styrene/isoprene/butadiene, NBR, terpolymers of acrylonitrile, butadiene and styrene and blends thereof.

5. A vulcanizable rubber composition comprising (1) a natural or synthetic rubber, (2) a sulfur vulcanizing agent, (3) from about 0 to about 6 phr of a methylene donor and (4) from about 0.1 to about 30 phr of alpha-(2,4-dihydroxy)phenyl N-phenyl nitrone, 6. The composition of claim 5 wherein the methylene donor is selected from the group consisting of hexamethylene tetramine, hexamethoxymethyl melamine, lauryloxymethyl pyridinium chloride, ethyloxymethyl pyridinium chloride, trioxan hexamethylol melamine and paraformaldehyde.

7. The composition according to claim 5 wherein the methylene donor is selected from the general formula:

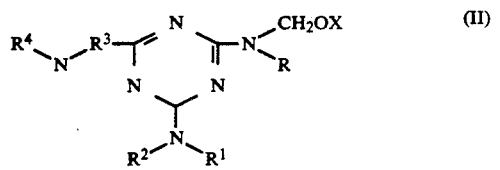

(II)

wherein X is an alkyl having from 1 to 8 carbon atoms, R, $R^1$, $R^2$, $R^3$ and $R^4$ are individually selected from the group consisting of hydrogen, an alkyl having from 1 to 8 carbon atoms, the group $-CH_2OX$ or their condensation products.

8. The composition of claim 5 wherein the methylene donor is selected from the group consisting of hexakis(methoxymethyl) melamine, N,N',N'''-trimethyl/N,N',N''-trimethylol melamine, hexamethylol melamine, N,N',N''-dimethylol melamine, N-methylol melamine, N,N'-dimethylol melamine, N,N',N'''-tris(methoxymethyl) melamine and N,N',N''-tributyl-N,N',N''-trimethylol melamine.

9. The composition of claim 5 wherein the weight ratio of methylene donor to the alpha-(2,4-dihydroxy)phenyl N-phenyl nitrone may range from about 1:10 to about 10:1.

10. The composition of claim 1 wherein the sulfur vulcanizing agent is selected from the group consisting of elemental sulfur, an amine disulfide, polymeric polysulfide or sulfur olefin adduct.

11. The composition of claim 10 wherein the sulfur vulcanizing agent ranges from about 0.1 to 7 phr.

12. The composition of claim 5 wherein the amount of the alpha-(2,4-dihydroxy)phenyl N-phenyl nitrone that is included in the sulfur vulcanizable rubber may range from about 2.0 to about 10 phr.

* * * * *